United States Patent
Garmi (10) Patent No.: US 12,405,394 B2
(45) Date of Patent: Sep. 2, 2025

(54) SYSTEM AND METHOD FOR SPECT RADIATION DETECTOR MODULE CALIBRATION BASED ON SUBJECT IMAGING EXAMINATION INFORMATION

(71) Applicant: GE Precision Healthcare LLC, Wauwatosa, WI (US)

(72) Inventor: Amatzia Garmi, Yodfat (IL)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 291 days.

(21) Appl. No.: 18/181,624

(22) Filed: Mar. 10, 2023

(65) Prior Publication Data

US 2024/0302551 A1   Sep. 12, 2024

(51) Int. Cl.
| | |
|---|---|
| G01T 7/00 | (2006.01) |
| A61B 6/03 | (2006.01) |
| A61B 6/58 | (2024.01) |
| G01T 1/164 | (2006.01) |
| G01T 1/36 | (2006.01) |

(52) U.S. Cl.
CPC ............. G01T 7/005 (2013.01); A61B 6/037 (2013.01); A61B 6/585 (2013.01); G01T 1/1647 (2013.01); G01T 1/365 (2013.01)

(58) Field of Classification Search
CPC ....... A61B 6/037; A61B 6/585; G01T 1/1647; G01T 1/365
See application file for complete search history.

(56) References Cited

U.S. PATENT DOCUMENTS

| | | | |
|---|---|---|---|
| 8,022,357 B2* | 9/2011 | Amir | G01T 1/1648 |
| | | | 250/361 R |
| 2017/0192104 A1* | 7/2017 | Bhattacharya | G01T 7/005 |
| 2017/0269240 A1* | 9/2017 | Shahar | G01T 1/249 |
| 2018/0110496 A1* | 4/2018 | Levy | A61B 6/037 |
| 2020/0301033 A1* | 9/2020 | Roth | G06T 7/80 |
| 2023/0069029 A1* | 3/2023 | Nguyen | G06V 20/00 |

* cited by examiner

*Primary Examiner* — David P Porta
*Assistant Examiner* — Casey Bryant
(74) *Attorney, Agent, or Firm* — Daugherty & Del Zoppo, Co. LPA (57) ABSTRACT

A method includes accumulating counts for each pixel in a set of pixels of one or more gamma cameras of a SPECT imaging system from a plurality of imaging examinations and each energy peak of each isotope used in the plurality of imaging examinations to produce an energy spectrum for each of the pixels at each of the energy peaks of each of the isotopes, determining, for the pixels and for the energy peaks, an energy calibration factor that converts an energy detected by each of the pixels to an energy of a corresponding energy peak and populating an energy map with the factors, and determining, for the pixels and for the energy peaks, a uniformity calibration factor that converts a number of counts detected by each of the pixels to a predetermined number of counts for a corresponding energy peak and populating a uniformity map with the factors.

20 Claims, 6 Drawing Sheets

SYSTEM AND METHOD FOR SPECT RADIATION DETECTOR MODULE CALIBRATION BASED ON SUBJECT IMAGING EXAMINATION INFORMATION

FIELD

The following generally relates to single photon emission computed tomography (SPECT), and more particularly for a SPECT radiation detector module calibration that is based on subject imaging examination information.

BACKGROUND

Single photon emission computed tomography (SPECT) imaging provides a non-invasive approach to collect functional information at the molecular and cellular level. In general, a SPECT imaging system includes a rotating gamma camera(s) that rotates around a patient positioned in an examination region, detects gamma rays emitted by a radiopharmaceutical administered to a patient in a region of interest of the patient over a plurality of angles, and outputs a signal indicative of the detected radiation (projection data), and a reconstructor that reconstructs the projection data to generate a two-dimensional (2-D) axial slice(s) and/or three-dimensional (3-D) volumetric imaging data of biological activity in the region of interest of the patient.

In general, the projection data is calibrated prior to reconstruction to compensate for position-dependent effects using values stored in look-up tables or maps. Examples of such calibrations include energy, uniformity and detector calibrations. To determine these calibrations, a uniform source (e.g., Cobalt-57 (Co-57), Technetium-99m (Tc-99m), etc.) is positioned in the examination region and data is acquired. For energy, the map includes a calibration factor for each pixel that converts the peak position measured by the pixel to the energy peak of the isotope. For uniformity, a flood image is generated, and the map includes a calibration factor for each pixel that is determined by dividing an average pixel count by the pixel count of a pixel. For the detector calibration, the map identifies pixels whose output values are replaced with values based on values of neighboring pixels because the pixel does not satisfy operating criteria.

In one instance, the initial calibration maps are created at the manufacturer. Thereafter, each day, prior to scanning a subject with the SPECT imaging system, a technician performs a calibration check to ensure that the existing calibration maps are still valid. For this, the technician positions a uniform source in the examination region, and the system evaluates the acquired data, including energy, uniformity and detector performance. Where the system determines that the existing calibration maps are within the defined limits and are still valid, the existing calibration maps are utilized that day for scanning. Where an existing calibration map(s) is determined to no longer be within the defined limits and are no longer valid, the technician performs a calibration procedure and updates the calibration map(s) to place the system back in calibration.

However, the imaging entity purchases the uniform source separately from the SPECT imaging system, which adds costs to the overall system. With a Co-57 source, the radioisotope continuously decays, and the uniform source has to be replaced (e.g., every 2-3 years), adding additional cost to the system. In addition, the literature indicates that a new uniform source of Co-57 usually contains small amounts of Co-56 and Co-58 contaminates, which have a shorter half-life than Co-57 and emit high energy gamma rays, which adversely affects the calibration. With a Tc-99m source, the technician adds liquid Tc-99m to a refillable container. The literature indicates that such a source is prone to distortion of the source, presence of air bubbles inside the source, poor mixing of the isotope within the source, and clumping or adhesion of the isotope to walls of the container. Furthermore, performing the daily calibration check and/or calibration procedure consumes technician time, and performing the calibration procedure may result in delaying scheduled examinations at least because the SPECT imaging system cannot be used to scan patients during the calibration. Furthermore, the uniform source exposes the technician to ionizing radiation, which can damage and kill cells.

In view of at least the foregoing, there is an unresolved need for an improved approach(s) for calibrating a gamma camera(s).

SUMMARY

Aspects of the application address the above matters, and others. This summary introduces concepts that are described in more detail in the detailed description. It should not be used to identify essential features of the claimed subject matter, nor to limit the scope of the claimed subject matter.

In one aspect, a computer-implemented method includes accumulating counts for each pixel in a set of pixels of one or more gamma cameras of a single photon emission tomography (SPECT) imaging system from a plurality of imaging examinations and each energy peak of each isotope used in the plurality of imaging examinations to produce an energy spectrum for each of the pixels at each of the energy peaks of each of the isotopes. The computer-implemented method further includes determining, for each of the pixels and for each of the energy peaks, an energy calibration factor that converts an energy detected by each of the pixels to an energy of a corresponding energy peak. The computer-implemented method further includes populating an energy calibration map for each energy peak with corresponding energy calibration factors. The computer-implemented method further includes determining, for each of the pixels and for each of the energy peaks, a uniformity calibration factor that converts a number of counts detected by each of the pixels to a predetermined number of counts for a corresponding energy peak. The computer-implemented method further includes populating a uniformity calibration map for each energy peak with corresponding uniformity calibration factors. The energy calibration map and the uniformity calibration map are utilized during scanning to calibrate pixel detected energy and pixel count uniformity.

In one embodiment, the computer-implemented method further comprises, prior to the accumulating of the counts, converting an energy detected by each of the pixels to an expected energy at a predetermined nominal reference temperature.

In one embodiment, the computer-implemented method further comprises employing an energy spectrum response function of the SPECT imaging system to convert the energy detected by each of the pixels to the expected energy.

In one embodiment, the energy calibration factor includes at least one of a gain and an offset for each of the pixels for each of the energy peaks.

In one embodiment, the computer-implemented method further comprises employing a pixel angular position and a pixel radial position of each of the pixels to identify a same pixel location for the plurality of imaging examinations.

In one embodiment, the computer-implemented method further comprises determining the predetermined number of counts for an energy peak of the energy peaks by determining an average number of counts of each of the pixels for the energy peak.

In one embodiment, the uniformity calibration factor includes a weight.

In one embodiment, the computer-implemented method further comprises employing a pixel angular position, a pixel radial position and a pixel swivel position of each of the pixels to identify a same pixel location and detection direction for the plurality of imaging examinations.

In one embodiment, the computer-implemented method further comprises identifying a sub-set of the pixels that fail to satisfy predetermined performance criteria and populating a detector calibration map with the identified sub-set of the pixels.

In one embodiment, the computer-implemented method further comprises replacing a value of each pixel in the sub-set of the pixels with a value based on values of neighboring pixels.

In one embodiment, the computer-implemented method further comprises identifying a pixel of the sub-set based on an energy calibration factor for the pixel.

In one embodiment, the computer-implemented method further comprises identifying a pixel of the sub-set based on a uniformity calibration factor for the pixel.

In one embodiment, the computer-implemented method further comprises identifying a pixel of the sub-set based on a signal to noise ratio for the pixel.

In another aspect, a system includes a memory that includes a calibration module with instructions for a SPECT calibration procedure and a processor configured to execute instructions and perform the SPECT calibration procedure. The SPECT calibration procedure includes accumulating counts for each pixel in a set of pixels of one or more gamma cameras of a single photon emission tomography (SPECT) imaging system from a plurality of imaging examinations and each energy peak of each isotope used in the plurality of imaging examinations to produce an energy spectrum for each of the pixels at each of the energy peaks of each of the isotopes. The SPECT calibration procedure further includes determining, for each of the pixels and for each of the energy peaks, an energy calibration factor that converts the energy detected by each pixel to an energy of each of the energy peaks. The SPECT calibration procedure further includes populating an energy calibration map for each energy peak with corresponding energy calibration factors. The SPECT calibration procedure further includes determining, for each of the pixels and for each of the energy peaks, a uniformity calibration factor that converts a number of counts detected by each of the pixels to a predetermined number of counts for each of the energy peaks. The SPECT calibration procedure further includes populating a uniformity calibration map for each energy peak with corresponding uniformity calibration factors.

In one embodiment, the processor and memory are part of the SPECT imaging system.

In one embodiment, the processor and memory are part of a computing system that is separate from the SPECT imaging system.

In one embodiment, the processor further converts an energy detected by each of the pixels to an expected energy at a predetermined nominal reference temperature, identifies a sub-set of the pixels that fail to satisfy predetermined performance criteria, and populates a detector calibration map with the identified sub-set of the pixels.

In another aspect, a computer readable medium is encoded with computer executable instructions. The computer executable instructions, when executed by a processor, cause the processor to accumulate counts for each pixel in a set of pixels of one or more gamma cameras of a single photon emission tomography (SPECT) imaging system from a plurality of imaging examinations and each energy peak of each isotope used in the plurality of imaging examinations to produce an energy spectrum for each of the pixels at each of the energy peaks of each of the isotopes. The computer executable instructions further cause the processor to determine, for each of the pixels and for each of the energy peaks, an energy calibration factor that converts the energy detected by each pixel to an energy of each of the energy peaks. The computer executable instructions further cause the processor to populate an energy calibration map for each energy peak with corresponding energy calibration factors determine, for each of the pixels and for each of the energy peaks, a uniformity calibration factor that converts a number of counts detected by each of the pixels to a predetermined number of counts for each of the energy peaks. The computer executable instructions further cause the processor to populate a uniformity calibration map for each energy peak with corresponding uniformity calibration factors.

In one embodiment, the computer executable instructions further cause the processor to convert an energy detected by each of the pixels to an expected energy at a predetermined nominal reference temperature.

In one embodiment, the computer executable instructions further cause the processor to identify a sub-set of the pixels that fail to satisfy predetermined performance criteria, and populate a detector calibration map with the identified sub-set of the pixels.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings in which like references indicate similar elements.

DETAILED DESCRIPTION

SPECT imaging calibrations for detected pixel energy, pixel uniformity and bad pixels currently are performed using a uniform source that is positioned in the examination region. Generally, since the source is uniform and does not include attenuating structure, the energy detected by the pixels should correspond to the energy of the isotope in the source and the number of counts detected by the pixels should all be within the same predetermined count range. The acquired data is analyzed and used to determine calibration factors that when applied to the detected energy and counts adjusts, if needed, the detected energy so that it corresponds to the isotope energy, and/or the counts so that the counts of all the pixels fall within the predetermined count range. The acquired data is also used to identify pixels with outputs outside of a predetermined operating range. As discussed above, there are disadvantages and/or shortcomings with the calibration procedure using a uniform source.

Described herein is a SPECT calibration approach that, in one instance, does not require and/or utilize a uniform source at least for pixel energy, pixel uniformity and bad pixel calibrations. Rather, the approach utilizes data and information from previously performed SPECT imaging examinations of patients. The data and information are used to accumulate enough counts for each pixel and for each isotope using counts from different imaging examinations acquired at different times and under different operation conditions (e.g., different temperatures, etc.) to perform the calibrations without compromising the quality of the calibrations. This includes considering information such as the 3-D location (x,y,z) of each pixel during each imaging examination for the energy calibration and, in addition, the direction each pixel faces for each detection for the uniformity calibration. The acquired data and/or the calibration factors for the energy and uniformity calibrations are used to identify bad pixels whose values are replaced with values based on neighboring pixels. The approach can be implemented on the SPECT imaging system and/or a computing device separate from the SPECT imaging system, and at a scheduled time(s) and/or continuously in the background.

Figure 1:
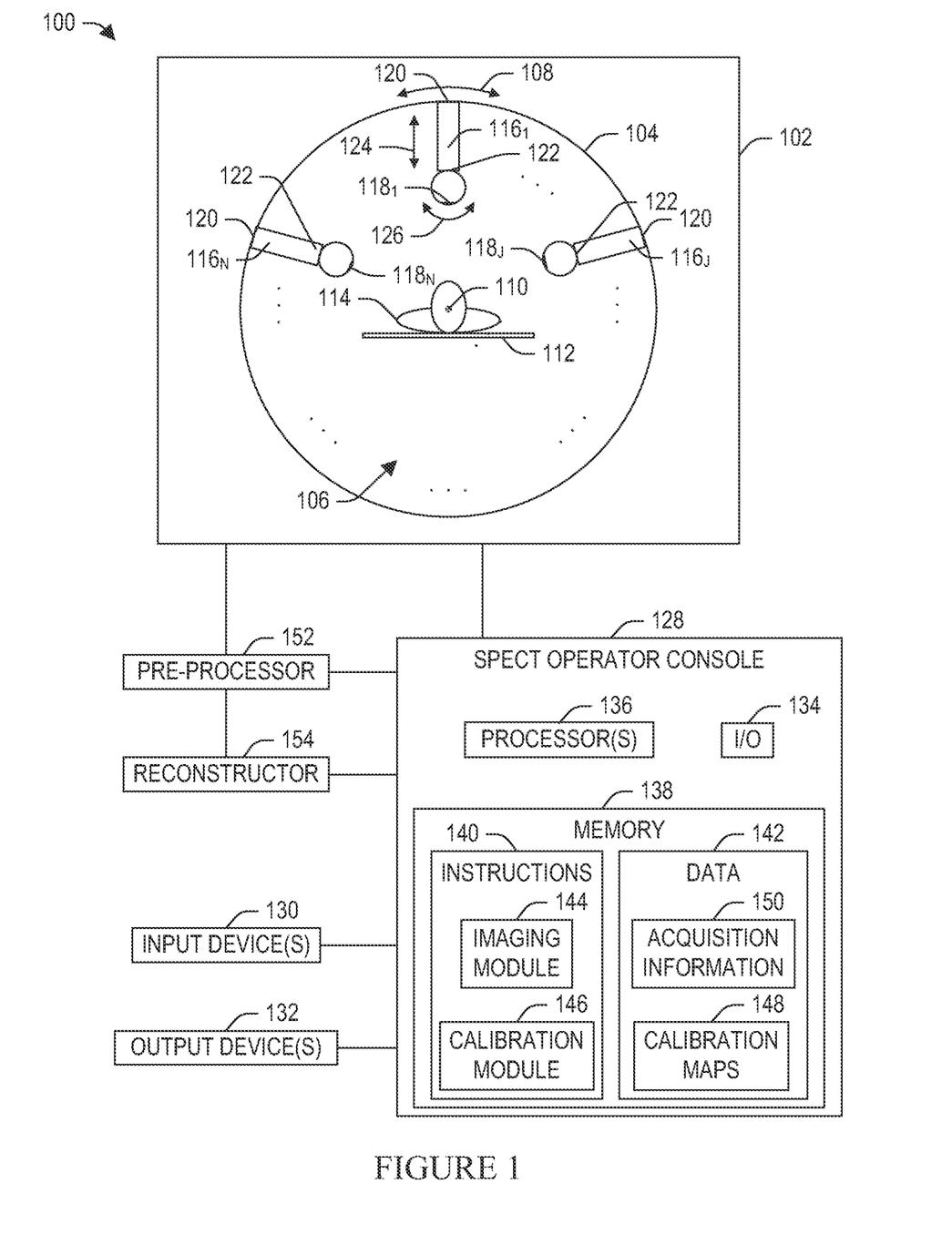
FIG. 1 schematically illustrates a non-limiting example of an imaging system configure for single photon emission computed tomography (SPECT) imaging, in accordance with an aspect of an embodiment(s) herein.

FIG. 1 schematically illustrates an example of an imaging system 100 configured for single photon emission computed tomography (SPECT) imaging. The imaging system 100 includes a gantry 102 and a frame 104. In one instance, the frame 104 includes an annular ring with an inner material free region (a bore, an aperture, an opening, etc.) that serves as an examination region 106, is rotatably supported by the gantry 102, e.g., via a bearing or the like, and is configured to rotate 108 around the examination region 106 about a rotational axis 110. In some instances, the gantry 102 is otherwise shaped such as "C," "H," "L" and/or otherwise shaped.

The imaging system 100 further includes a subject/object support 112 configured to support a subject 114 or object before, during and/or after an imaging examination. The support 112 as illustrated is configured to support a lying subject, where the subject 114 is loaded onto the support 112, the support 112 is moved into the examination region 106 such that a center of the subject 114 in an axial direction approximately aligns with the axis of rotation 110, an imaging examination is performed, and the support 112 is moved out of the examination region 106 to unload the subject 114. In some instances, the support 112 is configured to support a standing, a sitting, a leaning and/or otherwise positioned subject.

The imaging system 100 further includes N elongate support arms $116_1, \ldots, 116_j, \ldots, 116_N$ and N gamma cameras $118_1, \ldots, 118_j, \ldots, 118_N$, where N is an integer equal to or greater than one. Collectively, the N support arms $116_1, \ldots, 116_j, \ldots, 116_N$ are referred to herein as support arms 116, the N gamma cameras $118_1, \ldots, 118_j, \ldots, 118_N$ are referred to herein as gamma cameras 118. The support arms 116 include first ends 120 and second ends 122, which spatially oppose the first ends 120. The first ends 120 are supported by the rotating frame 104 and are angularly spaced apart from each other around the frame 104. The second ends 122 support the gamma cameras 118. The support arms 116 and gamma cameras 118 rotate in coordination with the rotating frame 104 about the rotational axis 110.

The support arms 116 are each configured to extend and retract radially 124 between the rotating frame 104 and the axis of rotation 110, where extending a support arm 116 moves the respective gamma camera 118 towards and closer to the axis of rotation 110 and hence the subject 114 and retracting a support arm 116 moves the respective gamma camera 118 away from the axis of rotation 110. Such movement can be provided via an actuator such as an actuator that converts rotary motion into linear displacement, an actuator with a hollow cylinder and a piston, and/or the like.

The gamma cameras 118 are moveably affixed to the second ends 122 of the support arms 116. In one instance, the gamma cameras 118 are configured to swivel 126 (sweep, pivot, rotate, or the like) at the second ends 122 of the support arms 116. The movement of the gamma cameras 118 can be independently controlled such that one gamma camera 118 can, e.g., swivel, while one or more of the remaining N−1 gamma cameras 118 remains stationary. However, one or more of the gamma cameras 118 can be moved in coordination with each other. Swiveling a gamma camera 118 focuses a detection surface of the gamma camera in the examination region 106 along particular paths of gamma rays from the subject 114.

In one instance, each of the gamma cameras 118 includes one or more modules or tiles (not visible), and each of the modules includes one or more radiation detectors (not visible), a collimator (not visible) and electronics (not visible). In one instance, the radiation detectors include a direct conversion material such as cadmium zinc telluride (CZT) with a plurality of pixels, the collimators include material free channels that allow radiation to pass unobstructed and septa therebetween configured to absorb and attenuate radiation impinging thereon, and the electronics (not visible) route electrical signals indicative of detected radiation off the gamma cameras 118. In general, incident gamma rays deposit their energy in the pixel crystal lattice generating pairs of charge carriers, an applied electric field collects the charge carriers to produce a current pulse, and, since, the current pulse comes from a single pixel, its position is known. The gamma cameras 118 may be different sizes and/or shapes with respect to each other.

A computing system, e.g., a computer, a workstation, a server, or the like) serves as a SPECT operator console 128. The SPECT operating console 128 includes an input device(s) 130 such as a keyboard, mouse, touchscreen, microphone, etc., an output device(s) 132 includes a human readable device such as a display monitor or the like, and input/output (I/O) 134 for sending and/or receiving signals and/or data. The SPECT operator console 128 further includes a processor(s) 136 such as a microprocessor (μP), a central processing unit (CPU), etc., and computer readable storage medium (memory) 138, which includes non-transitory medium and excludes transitory medium (signals, carrier waves, and the like).

The memory 138 is embedded or encoded with computer executable instructions (instructions) 140 and/or data 142, and the processor(s) 136 is configured to execute at least one of the computer executable instructions 140, employ and/or create the data 142, etc. The computer executable instructions 140 include an imaging module 144. The imaging module 144 includes instructions for presenting a user interface for planning and/or scanning subjects or objects. These instructions include instructions, e.g., for controlling the rotation 108 of the frame 104 and hence the gamma cameras 118, the radial position 124 of the gamma cameras 118, the swiveling 126 of the gamma cameras 118, etc.

The computer executable instructions 140 further include a calibration module 146, and the data 142 includes detector module calibration maps 148 and acquisition information 150. The calibration module 146 includes instructions for performing a detector module calibration and updating the detector module calibration maps 148, if needed. Briefly turning to FIG. 2, the calibration maps 148 include at least an energy map 202 with an energy calibration factor for each pixel, a uniformity map 204 with a uniformity calibration factor for each pixel, and detector map 206 that identifies pixels whose output values are to be replaced. Returning to FIG. 1, the calibration module 146 employs the acquisition information 150 to perform the calibration and generate data for the calibration maps 148.

As described in greater detail below, the acquisition information 150 includes patient SPECT imaging examination information. In one instance, using such information to generate the calibration maps 148 mitigates performing a calibration check and/or procedure using a uniform source and, hence, the disadvantages and/or shortcomings therewith. In one instance, the calibration module 146 performs a calibration at one or more pre-determined times throughout the day, e.g., before a first scheduled patient of the day is scanned, during the period when the technician is at lunch and/or on break, when the imaging system 100 is idle, etc. In another instance, the calibration module 146 runs in the background and performs a calibration when new acquisition information becomes available for the calibration, e.g., after an imaging examination. The calibration module 146 may automatically perform a calibration and/or performs a calibration in response to a user input invoking the calibration.

Figure 2:
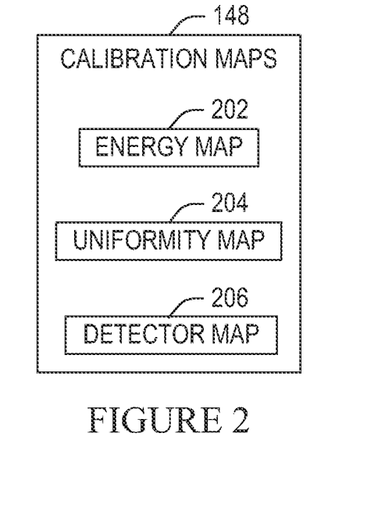
FIG. 2 schematically illustrates a non-limiting example of SPECT imaging system calibration maps, in accordance with an aspect of an embodiment(s) herein.

A pre-processor 152 receives the projection data generated by the gamma cameras 118 and calibrates the projection data based the calibration maps 148. In general, the pre-processor 152, for each pixel, looks up a pixel position in the energy map 202 and adjusts the measured peak energy for the pixel for shifts via the calibration factor, which includes a gain and an offset, thereby converting the detected peak energy to the actual energy peak, for each isotope used in each of the imaging examinations. The pre-processor 152 then looks up the pixel position in the uniformity map 204 and multiples the corresponding uniformity calibration factor, which includes a gain, with the counts detected by the pixel to calibrate the pixel, for each isotope used in each of the imaging examinations. The pre-processor 152 also replaces the values of the pixels identified in the detector map 206 as a "bad" pixel with values based on values of neighboring pixels.

A reconstructor 154 reconstructs the calibrated projection data. Suitable reconstruction algorithms include a filtered backprojection algorithm, an iterative algorithm, etc. The reconstructor 154 reconstructs a 2-D axial slice(s) and/or 3-D volumetric imaging data. The 2-D axial slice(s) and/or 3-D volumetric imaging data can be visually presented via a display monitor of the output device(s) 132, filmed via a filmer of the output device(s) 132, transferred to a cloud resource, a server, a workstation, a Radiology Information System (RIS), a Hospital Information System (HIS), an electronic medical record (EMR), and/or a Picture Archiving and Communications System (PACS), etc.

Figure 3:
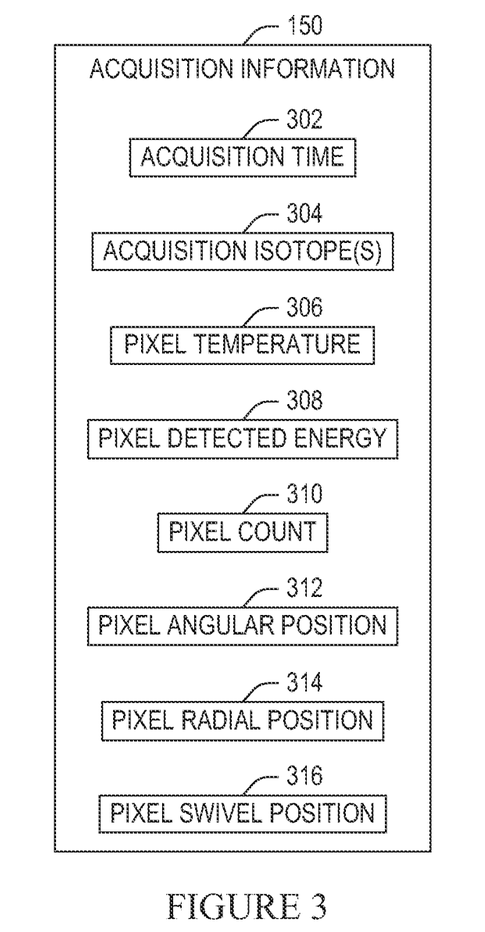
FIG. 3 schematically illustrates a non-limiting example of SPECT imaging system acquisition data and settings, in accordance with an aspect of an embodiment(s) herein.

As briefly discussed above, the calibration module 146 employs the acquisition information 150 to perform the calibration. Turning to FIG. 3, an example of the acquisition information 150 is schematically illustrated. The acquisition information 150 includes, for each imaging acquisition, an acquisition time 302, an acquisition isotope(s) 304, a pixel temperature 306 of each pixel (e.g., as determined by a temperature sensor of each detector module), pixel detected energy 308 for each pixel for each isotope, a number of counts detected by each pixel (pixel count) 310 for each isotope, a pixel angular position 312 of each pixel, a pixel radial position 314 of each pixel, and a pixel swivel position 316 of each pixel. The acquisition information 150 can be collected over the course of a day, a sub-portion of a day, or longer, e.g., over days. The acquisition information 150 can be stored separately, in a single data structure/file, in multiple data structure/files, etc.

Figure 4:
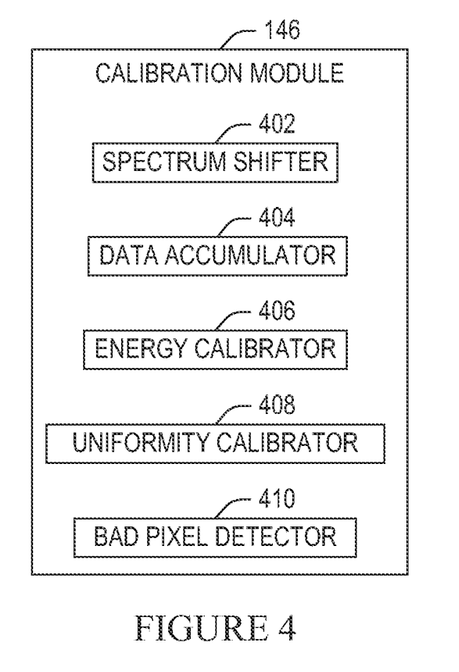
FIG. 4 schematically illustrates a non-limiting example of SPECT imaging system calibration modules, in accordance with an aspect of an embodiment(s) herein.

Turning to FIG. 4, an example of the calibration module 146 is schematically illustrated. The calibration module 146 includes a spectrum shifter 402. The spectrum shifter 402 adjusts the energy detected by each pixel (i.e. the pixel detected energy 308) in the acquisition information 150 based on the corresponding pixel temperature 306 in the acquisition information 150. As discussed herein, the temperature of pixel during an imaging examination is measured by a temperature sensor of a detector module of the pixel. In general, SPECT imaging system manufacturer measures an energy spectrum response function of their system by measuring the energy detected by each pixel for a given source at different temperatures and provides this information to their customers. Based on the energy spectrum response function, the spectrum shifter 402 converts the pixel detected energy 308 of each pixel to an expected energy for a predetermined nominal reference temperature.

By way of non-limiting example, the measured energy spectrum response function of a SPECT imaging system may indicate that every one degree of temperature change in a detector module will result in a 0.2 keV change in the measured energy. With this example, for a nominal reference temperature of eighteen degrees Celsius (18° C.), the energy spectrum for a pixel in a module with a temperature of twenty degrees Celsius (20° C.) would be adjusted down by 0.4 keV, and the energy spectrum for a pixel in a module with a temperature of seventeen degrees Celsius (17° C.) would be adjusted up by 0.2 keV. In another instance, the energy spectrum response function is non-linear. Generally, the temperature in an examination room tends to vary over the course of a day due to, e.g., heat dissipation from electronics, humans, etc. in the room. The measured energy spectrum is shifted to reduce a variation in the energy spectrum when merging counts together. In another instance, the spectrum shifter 402 is omitted, e.g., where the temperature change is within a predetermined window.

The calibration module 146 further includes a data accumulator 404. The data accumulator 404 accumulates counts for each pixel for each energy peak of interest based on the information in the acquisition information 150, including the acquisition isotope(s) 304, the pixel detected energy 308, the pixel count 310, the pixel angular position 312, and the pixel radial position 314. By way of non-limiting example, where the counts for imaging examinations are accumulated over a course of a day, the data accumulator 404 will accumulate pixel counts for each pixel for each energy peak corresponding to each isotope used for the imaging examinations that day beginning with the most recently acquired counts. The pixel swivel position 316 is not utilized for the count accumulation; the pixel 3-D location identifies the pixel, and the direction the pixel faces does not impact the pixel 3-D location.

The number of accumulated counts is checked to determine whether there are enough accumulated counts to sufficiently recognize peaks, e.g., a number of counts that would be used for a uniform source calibration. If it is determined that the number of accumulated counts is not enough to sufficiently recognize peaks, counts from a previous day(s) may be included in the accumulation. In general, the next available most recently acquired counts would be included in the accumulation. In one instance, to determine whether there are enough accumulated counts, the counts about a peak are summed and the peak height is compared to a pre-determined count threshold (e.g., 500), which is utilized to determine whether there are enough counts. A result of the accumulation of counts is a raw energy spectrum for each pixel for each isotope using the most recently acquired counts.

The calibration module 146 further includes an energy calibrator 406. The energy calibrator 406 determines energy calibration factors for each pixel for each energy peak of interest based on the information in the acquisition information 150, including the pixel detected energy 308 and the acquisition isotope(s) 304. The calibration factor, for a pixel, converts the peak position measured by the pixel to the actual energy peak (e.g., in keV). In one instance, the calibration factor includes a gain and an offset for each pixel. The calibration module 146 populates or updates the energy map 202 of the calibration maps 148 with the energy calibration factors. Where multiple or at least two isotopes are utilized concurrently, the energy calibrator 406 can determine the energy calibration factors for each isotope as long as the energy peaks of the isotopes are known.

In one instance, where the calibration is successful, the calibration module 146 displays a message via a calibration user interface on a display monitor of the output device(s) 132 indicating the energy map 202 was successfully updated, updates a calibration log file with information indicating the energy map 202 was successfully updated, etc. Where the calibration was not successful, the calibration module 146 may display a message indicating the shifts are out of range, a significant degradation was identified, etc., and that further action should be taken by the technician and/or service, update the calibration log file accordingly, etc. The energy calibration results and/or energy map 202 history can be saved for evaluation of the imaging system 100 and/or gamma cameras 118.

The calibration module 146 further includes a uniformity calibrator 408. The uniformity calibrator 408 determines energy calibration factors (e.g., weights) for each pixel for each energy peak of interest based on the information in the acquisition information 150, including the pixel angular position 312, the pixel radial position 314, and the pixel swivel position 316. The pixel angular position 312 and the pixel radial position indicate the 3-D position of each pixel. The pixel swivel position 316 will ensure that gamma rays traversing a similar or same path through the anatomy and attenuated by similar or the same anatomy in the patient are grouped together, as a camera 118 can be swiveled between two or more locations at a given angular and radial location pair, with each focused at a different gamma ray path from the patient. The uniformity calibrator 408 compares counts at the same position and focus for different pixels and different points in time.

Generally, based on the pixel angular, radial and swivel positions 312, 314 and 316 for each gamma camera 118, overlaps between pixels can be calculated, and the pixels that are overlapping are compared and will have a relative uniformity value with respect to each other. The acquisition time 302 and the acquisition isotope(s) 304 are used to compensate for radioactive decay, i.e. the decrease in count rate from the uniform source in time, e.g., depending on a half-life value of each specific isotope(s). The uniformity calibrator 408 computes an average count value for counts within a given count window, and determines a uniformity calibration factor for a pixel by dividing the average count value by the pixel count of the pixel, for each isotope. For example, where the average count is one hundred (100), the calibration factor for a pixel with a count of ninety (90) will scale the pixel count of 90 to 100, and the calibration factor for a pixel with a count of one hundred five (105) will scale the pixel count of 105 to 100. The calibration module 146 populates or updates the uniformity map 204 of the calibration maps 148 with the uniformity calibration factor.

The calibration module 146 further includes a bad pixel detector 410. The bad pixel detector 410 identifies pixels with outputs that do not satisfy pre-determined operating criteria, e.g., noisy pixels, pixels with no output, pixels with an unstable output, etc. In one instance, the bad pixel detector 410 identifies a bad pixel based on the energy and/or the uniformity calibration factors for the pixel. For example, the bad pixel detector 410 identifies a pixel as a bad pixel where the energy (and/or the uniformity) calibration factor is high (e.g., based on a threshold value, e.g., a 3× multiplication factor), which would result in too much of an increase in noise. In another instance, the bad pixel detector 410 identifies a pixel as a bad pixel where the number of counts around the energy peak is higher or lower than expected (e.g., based on a threshold). In another instance, the bad pixel detector 410 identifies a pixel as a bad pixel based on a signal to noise ratio for the pixel.

In one instance, the value of a pixel identified as a bad pixel is replaced with an average of the values of two or more direct neighboring pixels. In another instance, a least gradient approach is utilized to determine the pixel value, where a box is centered at the bad pixel and a new value of the bad pixel is derived from the average of the neighboring pixels along the direction in which the gradient is the least. In another instance, an interpolation algorithm is utilized to determine the value for the bad pixel. The calibration module 146 populates or updates the detector map 206 of the calibration maps 148 with the identified bad pixels. In another instance, the value of a bad pixel is corrected for during reconstruction. For example, a bad pixel(s) can be identified as a "no-data" pixel to the reconstructor 154, which, during reconstruction of an image from the projection, can employ a reconstruction algorithm that corrects for pixels with no data as input.

As discussed herein, the calibration maps 128 are utilized to calibrates projection data prior to reconstruction. In one instance, the approach described herein is employed without any data acquired during a uniform source calibration check and/or procedure. In another instance, the approach described herein can be used in connection with a uniform source calibration check and/or procedure and/or data acquired thereby. In addition, although the approach as described herein populates all three of the maps 128 (i.e. the energy map 202, the uniformity map 204 and the detector map 206), it is to be appreciated that the calibration module 146 can be used to populate only the energy map 202 and not the uniformity map 204 and the detector map 206, only the energy map 202 and the uniformity map 204 and not the detector map 206, etc.

Figure 5:
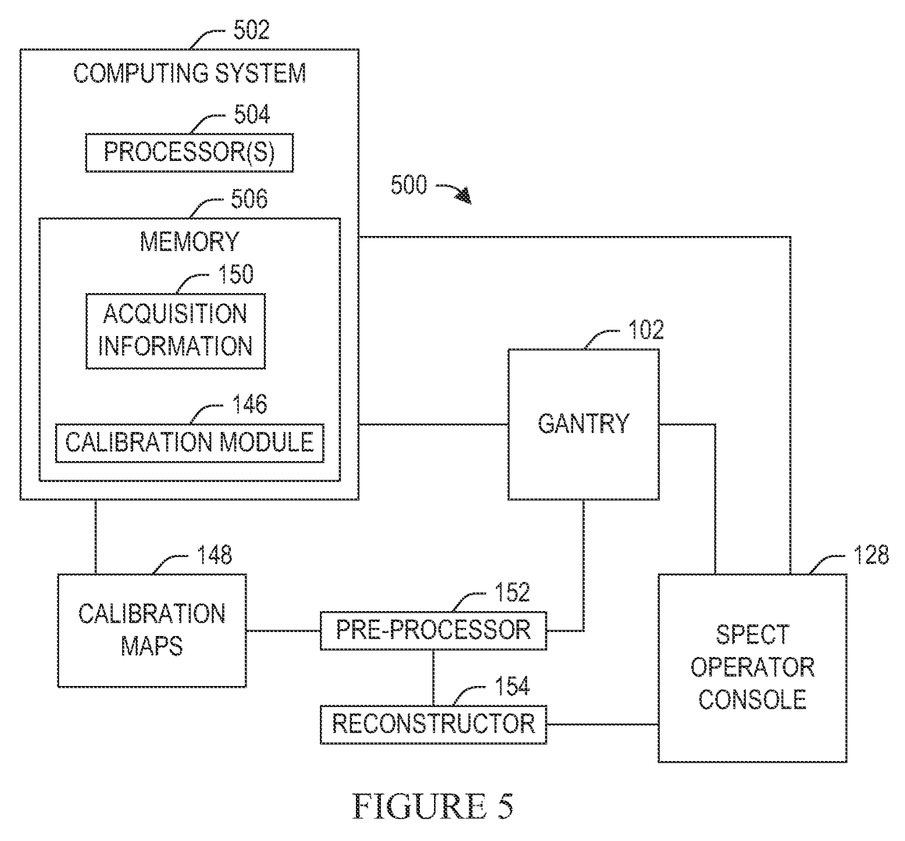
FIG. 5 schematically illustrates another non-limiting example of an imaging system configure for single photon emission computed tomography (SPECT) imaging, in accordance with an aspect of an embodiment(s) herein.

FIG. 5 schematically illustrates example of an imaging system 500 configured for SPECT imaging. The imaging system 500 is similar to the imaging system 100 except that the calibration module 146 is located in a computing system 502, which is separate and remote from the SPECT operator console 128, instead of in the SPECT operator console 128 as shown in connection with the imaging system 100 of FIG. 1. The computing system 502 is in operative communication with the imaging system 500 and receives the acquisition information 150 therefrom. The calibration maps 148 can be stored in the computing system 502, in the SPECT operator console 128 of the imaging system 500, and/or in other memory.

The computing system 502, similar to the SPECT console 128, can be a computer, a workstation, a server, or the like, with a processor 504 and computer readable storage medium (memory) 506 encoded or embedded with computer readable and/or executable instructions. The computing system 502 can be in the same room as the SPECT operator console 128, the examination room, another location within the imaging facility, in another facility, in the cloud, etc., as a single apparatus or distributed across multiple apparatuses and/or locations, etc. In another instance, the calibration module 146 is located in both the computing system 502 and the SPECT operator console 128.

Figure 6:
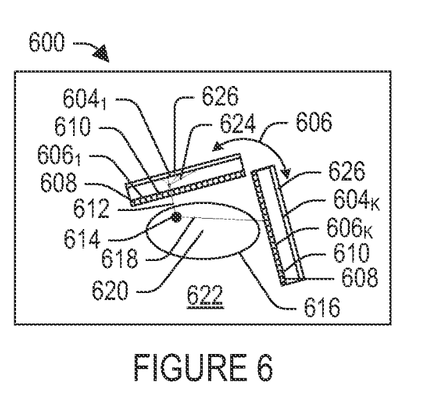
FIG. 6 schematically illustrates another non-limiting example of an imaging system configure for single photon emission computed tomography (SPECT) imaging, in accordance with an aspect of an embodiment(s) herein.

FIG. 6 schematically illustrates an imaging system 600 configured for SPECT imaging. The imaging system 600 is similar to the imaging system 100 or 500, except that instead of having the ring shaped frame 104 with the gamma cameras 118 (FIG. 1), the imaging system 600 includes k gamma cameras $604_1, \ldots, 604_k$, with k collimator $606_1, \ldots, 606_k$, where k is an integer equal to or greater than one (two are shown for sake of explanation). Collectively, the k gamma cameras $604_1, \ldots, 604_k$ are referred to herein as gamma cameras 604, and the k collimators $606_1, \ldots, 606_k$ are referred to herein as collimators 606. The collimators 606 include septa 608 spatially arranged to provide channels 610 that pass gamma rays 612 emitted by a radiopharmaceutical 614 in a patient 616, where the septa 608 are configured to absorb and attenuate radiation 618 impinging thereon. The septa 608 can be parallel (as illustrated), converging, diverging, pinhole, etc.

The gamma cameras 604 can be positioned 90 degrees with respect to each other (as illustrated) or otherwise, e.g., 45, 60, 180, etc. degrees. The gamma cameras 604 are configured to rotate 606 around an axis of rotation 620 about the patient 616 in an examination region 622 and detect gamma rays, e.g., the gamma ray 614, passing through the channels 610. In one instance, the gamma cameras 604 include a thallium-doped sodium iodide (NaI (TI)) scintillation crystal that converts gamma rays to light photons 624 and a bank of photomultiplier tubes (PMTs) 626 that convert the light photons into electrical signals indicative of an energy of the gamma rays or a pixelated NaI (TI) scintillation crystal that converts gamma rays to the light photons 624 and the PMTs 626 or solid-state photodiode (PD) array that converts the light photons into electrical signals indicate of an energy of the gamma rays. The gamma cameras 604 are configured to acquire projections from a number of angles with respect to the examination region 622. The projection data is processed as discussed in connection with the imaging system 100.

Figure 7:
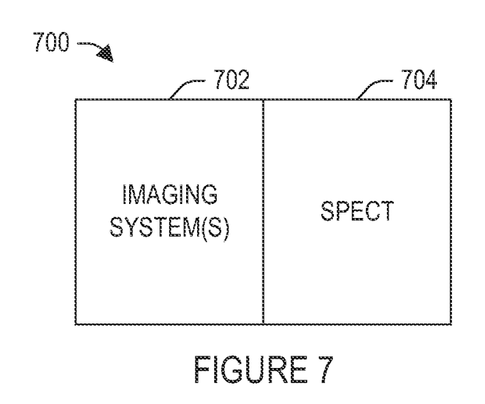
FIG. 7 schematically illustrates another non-limiting example of an imaging system configure for single photon emission computed tomography (SPECT) imaging, in accordance with an aspect of an embodiment(s) herein.

FIG. 7 schematically illustrates another example of an imaging system 700 configured for SPECT imaging. The imaging system 700 includes at least one of the imaging systems 100, 500 or 600 or another imaging system configured for SPECT imaging that uses the maps populated or updated by the calibration module 146 and an imaging system configured for computed tomography (CT) imaging or magnetic resonance (MR) imaging. Such systems have been referred to as combination or hybrid SPECT-CT and SPECT-MR imaging systems.

Figure 8:
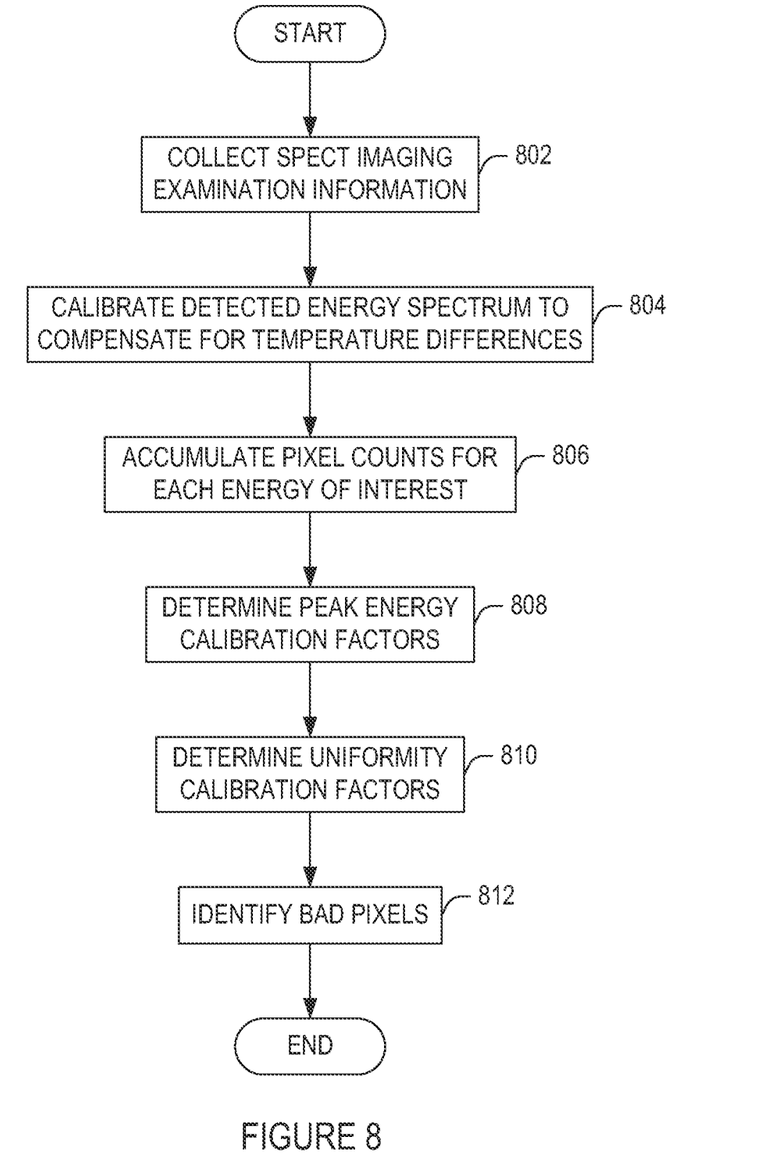
FIG. 8 illustrates a non-limiting example of a flow chart for a computer-implemented method, in accordance with an embodiment(s) herein.

FIG. 8 illustrates a non-limiting example of a flow chart for a computer-implemented method. It is to be appreciated that the ordering of the acts in the method is not limiting. As such, other orderings are contemplated herein. In addition, one or more acts may be omitted, and/or one or more additional acts may be included.

At 802, information regarding SPECT imaging examinations over a predetermined time period is collected, including a time of each imaging examination, the isotope(s) used for each imaging examination, the temperatures of the detector modules for each imaging examination, the energy detected by each pixel for each imaging examination, the number of counts for each pixel for each imaging examination, the rotational, radial and sweep positions of each detector module for each imaging examination, etc., as described herein and/or otherwise.

At 804, the energy detected by each pixel for each study is calibrated to compensate for temperature differences based on the collected temperatures of the detector modules for each imaging examination and an energy spectrum response function of the SPECT imaging system, as described herein and/or otherwise. At 806, the energy calibrated counts are accumulated for each pixel and isotope over the predetermined time period, or the predetermined time period plus an earlier predetermined time period(s), as described herein and/or otherwise.

At 808, an energy calibration factor is determined for each pixel for each isotope and stored in an energy map, as described herein and/or otherwise. At 810, a uniformity calibration factor is determined for each pixel for each isotope and stored in a uniformity map, as described herein and/or otherwise. At 812, bad pixels are identified and stored in a bad detector map, as described herein and/or otherwise. The energy calibration, uniformity calibration and bad detector maps are utilized during scanning to calibrate SPECT projection data and are updated, as described herein and/or otherwise.

Figure 9:
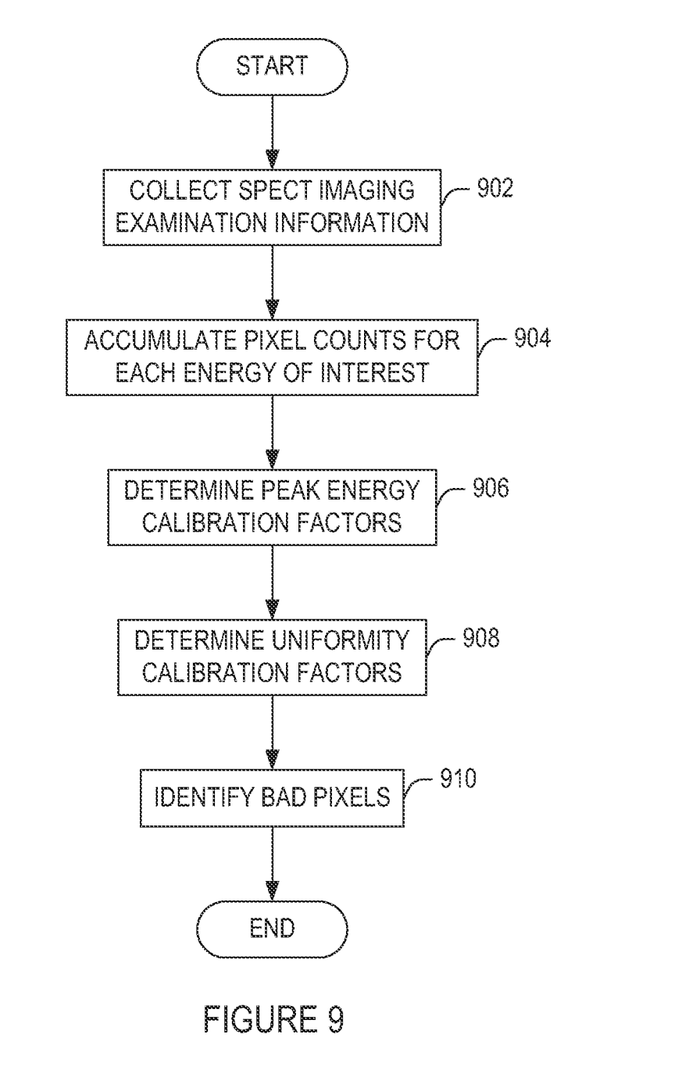
FIG. 9 illustrates another non-limiting example of a flow chart for a computer-implemented method, in accordance with an embodiment(s) herein.

FIG. 9 illustrates a non-limiting example of a flow chart for a computer-implemented method. It is to be appreciated that the ordering of the acts in the method is not limiting. As such, other orderings are contemplated herein. In addition, one or more acts may be omitted, and/or one or more additional acts may be included.

At 902, information regarding SPECT imaging examinations over a predetermined time period is collected, including a time of each imaging examination, the isotope(s) used for each imaging examination, the temperatures of the detector modules for each imaging examination, the energy detected by each pixel for each imaging examination, the number of counts for each pixel for each imaging examination, the rotational, radial and sweep positions of each detector module for each imaging examination, etc., as described herein and/or otherwise. At 904, the collected counts are accumulated for each pixel and isotope over the predetermined time period, or the predetermined time period plus an earlier predetermined time period(s), as described herein and/or otherwise.

At 906, an energy calibration factor is determined for each pixel for each isotope and stored in an energy map, as described herein and/or otherwise. At 908, a uniformity calibration factor is determined for each pixel for each isotope and stored in a uniformity map, as described herein and/or otherwise. At 910, bad pixels are identified and stored in a bad detector map, as described herein and/or otherwise. The energy calibration, uniformity calibration and bad detector maps are utilized during scanning to calibrate SPECT projection data and are updated, as described herein and/or otherwise.

Figure 10:
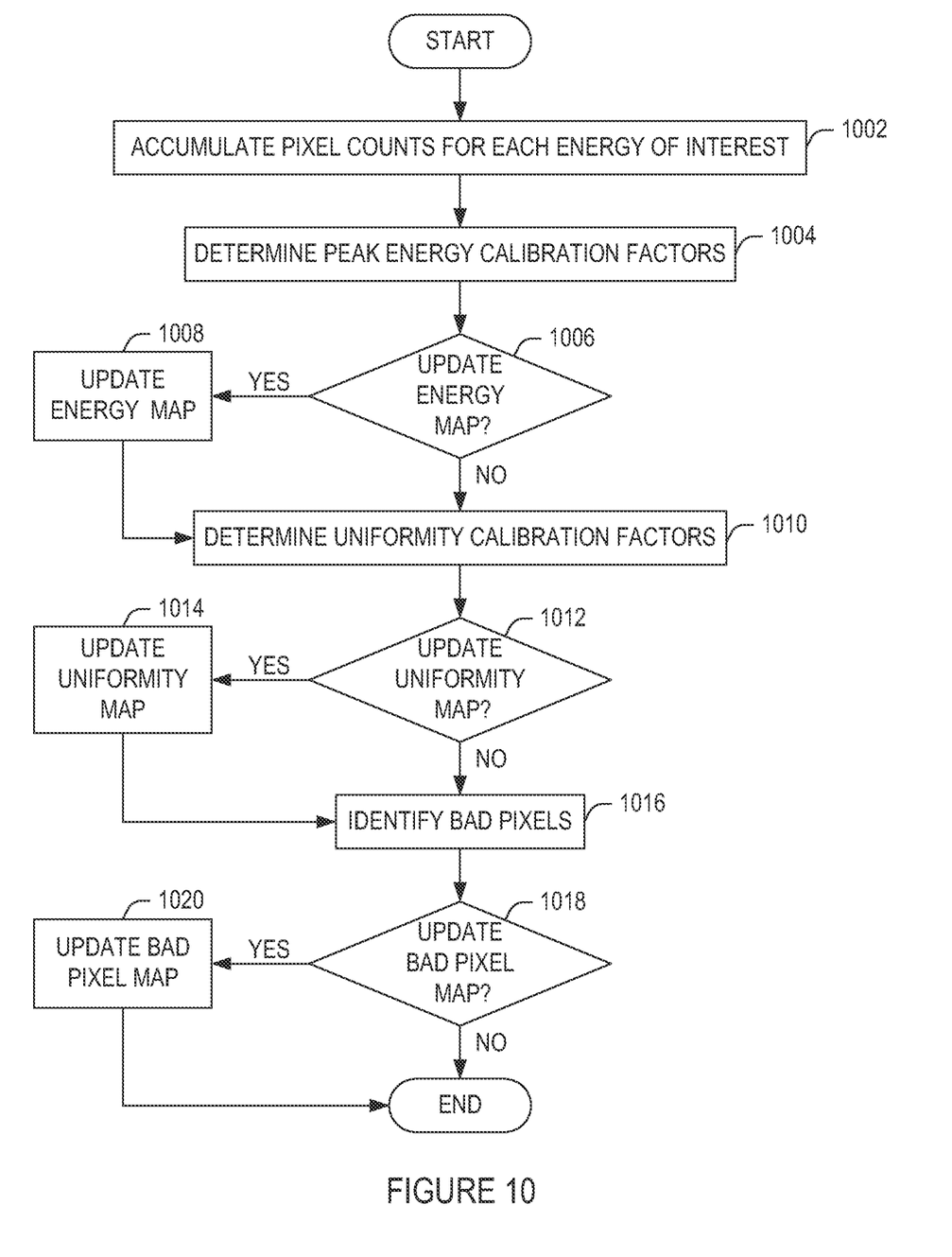
FIG. 10 illustrates another non-limiting example of a flow chart for a computer-implemented method, in accordance with an embodiment(s) herein.

FIG. 10 illustrates a non-limiting example of a flow chart for a computer-implemented method. It is to be appreciated that the ordering of the acts in the method is not limiting. As such, other orderings are contemplated herein. In addition, one or more acts may be omitted, and/or one or more additional acts may be included.

At 1002, collected energy counts are accumulated for each pixel and isotope over a predetermined time period or the predetermined time period plus an earlier predetermined time period(s), as described herein and/or otherwise. The energy counts can be variously collected. For example, the counts can be collected based on a combination of one or more of the approaches described in connection with FIG. 8, FIG. 9, a uniform source, and/or other approach(s).

At 1004, an energy calibration factor is determined for each pixel for each isotope, as described herein and/or otherwise. At 1006, it is determined if an existing energy map needs to be updated. For instance, if the differences between the determined energy calibration factors and the energy calibration factors in the map satisfies a predetermined threshold, which indicates the existing energy calibration factors are still valid, the energy map is not updated, and the existing energy map is utilized. However, in some instances, the energy map is still updated even where the threshold is satisfied. If the differences between the determined energy calibration factors and the energy calibration factors in the map fail to satisfy the predetermined threshold, which indicates the existing energy calibration factors are no longer valid, then at 1008, the energy map is updated.

At 1010, a uniformity calibration factor is determined for each pixel for each isotope, as described herein and/or otherwise. At 1012, it is determined if an existing uniformity map needs to be updated. For instance, if the differences between the determined uniformity calibration factors and the uniformity calibration factors in the map satisfies a predetermined threshold, which indicates the existing uniformity calibration factors are still valid, the uniformity map is not updated, and the existing uniformity map is utilized. However, in some instances, the uniformity map is still updated even where the threshold is satisfied. If the differences between the determined uniformity calibration factors and the uniformity calibration factors in the map fail to satisfy the predetermined threshold, which indicates the existing uniformity calibration factors are no longer valid, then at 1014, the uniformity map is updated.

At 1016, bad pixels are identified, as described herein and/or otherwise. At 1018, it is determined if an existing bad pixel map needs to be updated. For instance, if the differences between the determined bad pixels and the bad pixels in the map satisfies a predetermined threshold, which indicates the existing bad pixels are still valid, the bad pixel map is not updated, and the existing bad pixel is utilized. However, in some instances, the bad pixel map is still updated even where the threshold is satisfied. If the differences between the determined bad pixels and the bad pixels in the map fail to satisfy the predetermined threshold, which indicates the existing bad pixels are no longer valid, then at 1020, the bad pixel map is updated.

The energy calibration, uniformity calibration and bad detector maps (updated or not) are utilized during scanning to calibrate SPECT projection data and are updated, as described herein and/or otherwise.

The above method(s) can be implemented by way of computer readable instructions, encoded, or embedded on the computer readable storage medium, which, when executed by a computer processor, cause the processor to carry out the described acts or functions. Additionally, or alternatively, at least one of the computer readable instructions is carried out by a signal, carrier wave or other transitory medium, which is not computer readable storage medium.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include such additional elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer". The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present disclosure. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. A computer-implemented method, comprising:
   accumulating counts for each pixel in a set of pixels of one or more gamma cameras of a single photon emission tomography (SPECT) imaging system from a plurality of imaging examinations of patients and each energy peak of each isotope used in the plurality of imaging examinations of patients to produce an energy spectrum for each of the pixels at each of the energy peaks of each of the isotopes;
   determining, for each of the pixels and for each of the energy peaks, an energy calibration factor that converts an energy detected by each of the pixels to an energy of a corresponding energy peak;
   populating an energy calibration map for each energy peak with corresponding energy calibration factors;
   determining, for each of the pixels and for each of the energy peaks, a uniformity calibration factor that converts a number of counts detected by each of the pixels to a predetermined number of counts for a corresponding energy peak; and
   populating a uniformity calibration map for each energy peak with corresponding uniformity calibration factors,
   wherein the energy calibration map and the uniformity calibration map are utilized during scanning to calibrate pixel detected energy and pixel count uniformity.

2. The computer-implemented method of claim 1, further comprising, prior to the accumulating of the counts:
   converting an energy detected by each of the pixels to an expected energy at a predetermined nominal reference temperature.

3. The computer-implemented method of claim 1, further comprising:
   employing an energy spectrum response function of the SPECT imaging system to convert the energy detected by each of the pixels to the expected energy.

4. The computer-implemented method of claim 1, wherein the energy calibration factor includes at least one of a gain and an offset for each of the pixels for each of the energy peaks.

5. The computer-implemented method of claim 1, further comprising:
   employing a pixel angular position and a pixel radial position of each of the pixels to identify a same pixel location for the plurality of imaging examinations of patients.

6. The computer-implemented method of claim 5, wherein the uniformity calibration factor includes a weight.

7. The computer-implemented method of claim 5, further comprising:
   employing a pixel angular position, a pixel radial position and a pixel swivel position of each of the pixels to identify a same pixel location and detection direction for the plurality of imaging examinations of patients.

8. The computer-implemented method of claim 1, further comprising:
determining the predetermined number of counts for an energy peak of the energy peaks by determining an average number of counts of each of the pixels for the energy peak.

9. The computer-implemented method of claim 1, further comprising:
identifying a sub-set of the pixels that fail to satisfy predetermined performance criteria; and
populating a detector calibration map with the identified sub-set of the pixels.

10. The computer-implemented method of claim 9, further comprising:
replacing a value of each pixel in the sub-set of the pixels with a value based on values of neighboring pixels.

11. The computer-implemented method of claim 9, further comprising:
identifying a pixel of the sub-set based on an energy calibration factor for the pixel.

12. The computer-implemented method of claim 9, further comprising:
identifying a pixel of the sub-set based on a uniformity calibration factor for the pixel.

13. The computer-implemented method of claim 9, further comprising:
identifying a pixel of the sub-set based on a signal to noise ratio for the pixel.

14. A system, comprising:
a memory that includes a calibration module with instructions for a SPECT calibration procedure; and
a processor configured to execute instructions and perform the SPECT calibration procedure, including:
accumulating counts for each pixel in a set of pixels of one or more gamma cameras of a single photon emission tomography (SPECT) imaging system from a plurality of imaging examinations of patients and each energy peak of each isotope used in the plurality of imaging examinations of patients to produce an energy spectrum for each of the pixels at each of the energy peaks of each of the isotopes;
determining, for each of the pixels and for each of the energy peaks, an energy calibration factor that converts the energy detected by each pixel to an energy of each of the energy peaks;
populating an energy calibration map for each energy peak with corresponding energy calibration factors;
determining, for each of the pixels and for each of the energy peaks, a uniformity calibration factor that converts a number of counts detected by each of the pixels to a predetermined number of counts for each of the energy peaks; and
populating a uniformity calibration map for each energy peak with corresponding uniformity calibration factors.

15. The system of claim 14, wherein the processor and memory are part of the SPECT imaging system.

16. The system of claim 14, wherein the processor and memory are part of a computing system that is separate from the SPECT imaging system.

17. The system of claim 14, wherein the processor further:
converts an energy detected by each of the pixels to an expected energy at a predetermined nominal reference temperature;
identifies a sub-set of the pixels that fail to satisfy predetermined performance criteria; and
populates a detector calibration map with the identified sub-set of the pixels.

18. A computer readable medium encoded with computer executable instructions, which, when executed by a processor, cause the processor to:
accumulate counts for each pixel in a set of pixels of one or more gamma cameras of a single photon emission tomography (SPECT) imaging system from a plurality of imaging examinations of patients and each energy peak of each isotope used in the plurality of imaging examinations of patients to produce an energy spectrum for each of the pixels at each of the energy peaks of each of the isotopes;
determine, for each of the pixels and for each of the energy peaks, an energy calibration factor that converts the energy detected by each pixel to an energy of each of the energy peaks;
populate an energy calibration map for each energy peak with corresponding energy calibration factors;
determine, for each of the pixels and for each of the energy peaks, a uniformity calibration factor that converts a number of counts detected by each of the pixels to a predetermined number of counts for each of the energy peaks; and
populate a uniformity calibration map for each energy peak with corresponding uniformity calibration factors.

19. The computer readable medium of claim 18, wherein the computer executable instructions further cause the processor to:
convert an energy detected by each of the pixels to an expected energy at a predetermined nominal reference temperature.

20. The computer readable medium of claim 18, wherein the computer executable instructions further cause the processor to:
identify a sub-set of the pixels that fail to satisfy predetermined performance criteria; and
populate a detector calibration map with the identified sub-set of the pixels.

* * * * *